(12) United States Patent
Okamoto et al.

(10) Patent No.: US 9,808,152 B2
(45) Date of Patent: Nov. 7, 2017

(54) ANTERIOR OCULAR SEGMENT OPTICAL COHERENCE TOMOGRAPHIC IMAGING DEVICE AND ANTERIOR OCULAR SEGMENT OPTICAL COHERENCE TOMOGRAPHIC IMAGING METHOD

(71) Applicant: Tomey Corporation, Nagoya-shi (JP)

(72) Inventors: Keiichiro Okamoto, Nagoya (JP); Risa Higashita, Nagoya (JP); Fushi Li, Nagoya (JP); Makoto Kojima, Nagoya (JP)

(73) Assignee: Tomey Corporation, Nagoya-Shi (JP)

( * ) Notice: Subject to any disclaimer, the term of this patent is extended or adjusted under 35 U.S.C. 154(b) by 0 days.

(21) Appl. No.: 15/179,511

(22) Filed: Jun. 10, 2016

(65) Prior Publication Data

US 2016/0360962 A1 Dec. 15, 2016

(30) Foreign Application Priority Data

Jun. 11, 2015 (JP) .................... 2015-117991

(51) Int. Cl.
| | |
|---|---|
| A61B 3/14 | (2006.01) |
| A61B 3/00 | (2006.01) |
| A61B 3/117 | (2006.01) |
| A61B 3/10 | (2006.01) |
| G06T 7/12 | (2017.01) |

(52) U.S. Cl.
CPC .......... *A61B 3/1176* (2013.01); *A61B 3/0025* (2013.01); *A61B 3/102* (2013.01); *A61B 3/117* (2013.01); *A61B 3/14* (2013.01); *G06T 7/12* (2017.01); *G06T 2207/10101* (2013.01); *G06T 2207/30041* (2013.01)

(58) Field of Classification Search
USPC ................................. 351/200–246
See application file for complete search history.

(56) References Cited

U.S. PATENT DOCUMENTS

| | | | |
|---|---|---|---|
| 8,992,016 B2 * | 3/2015 | Utsunomiya | A61B 3/0058 |
| | | | 351/206 |
| 2012/0320339 A1 * | 12/2012 | Yonezawa | A61B 3/102 |
| | | | 351/208 |
| 2015/0092162 A1 * | 4/2015 | Tsunehiro | A61F 2/145 |
| | | | 351/206 |

FOREIGN PATENT DOCUMENTS

| | | |
|---|---|---|
| JP | 2009142313 | 7/2009 |
| WO | 2007133964 | 11/2007 |

(Continued)

*Primary Examiner* — Mohammed Hasan
(74) *Attorney, Agent, or Firm* — Jeffrey D. Myers; Peacock Myers, P.C.

(57) ABSTRACT

An anterior ocular segment optical coherence tomographic imaging device and an anterior ocular segment optical coherence tomographic imaging method that can accurately analyze the shape of a crystalline lens by identifying the boundary of each layer of the crystalline lens in a tomographic image of an anterior ocular segment of a subject's eye, which is taken by optical coherence tomography. A layer boundary detector calculates brightness gradients from brightness values in a tomographic image of an anterior ocular segment of a subject's eye, which is taken by optical coherence tomography, in a depth direction of the tomographic image from a cornea to a retina, detect edges b1, b2, b3, and b4 that are larger than a predetermined threshold, and identify a boundary of each layer of the crystalline lens L from positions of the edge b1, b2, b3, and b4.

12 Claims, 9 Drawing Sheets

(56) References Cited

FOREIGN PATENT DOCUMENTS

| WO | 2011114686 | 9/2011 |
|----|------------|--------|
| WO | 2013187361 | 12/2013 |

* cited by examiner

FIG. 7A
FIG. 7B
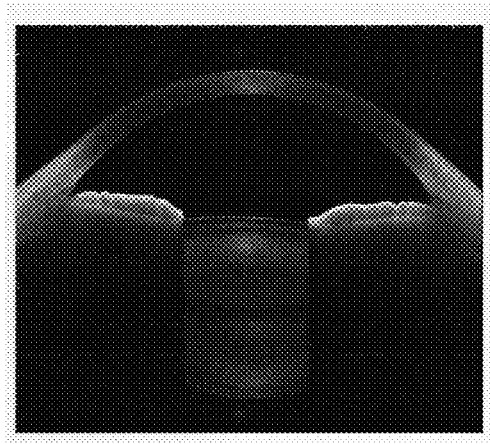
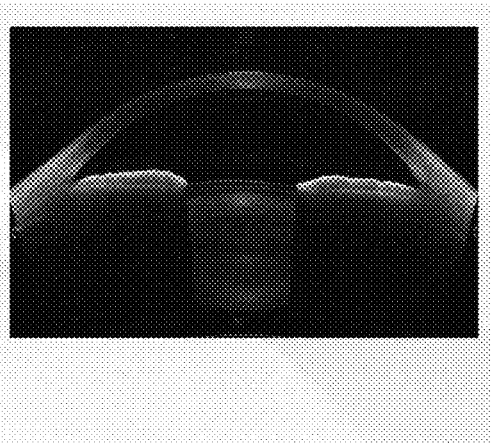

ANTERIOR OCULAR SEGMENT OPTICAL COHERENCE TOMOGRAPHIC IMAGING DEVICE AND ANTERIOR OCULAR SEGMENT OPTICAL COHERENCE TOMOGRAPHIC IMAGING METHOD

BACKGROUND

1. Technical Field

The present invention relates to an anterior ocular segment optical coherence tomographic imaging device and an anterior ocular segment optical coherence tomographic imaging method that take a tomographic image of an anterior ocular segment including a crystalline lens of a subject's eye.

2. Related Art

Examples of ophthalmologic inspection equipment include an optical coherence tomographic imaging device that images a tomography image of an eye (eyeball) of a subject using Optical Coherence Tomography (OCT). The optical coherence tomographic imaging device is roughly classified into a time domain type (TD-OCT) and a Fourier domain type (FD-OCT).

According to TD-OCT, a beam from a light source is divided into a measurement light and a reference light using a beam splitter, and a reference mirror mechanically scan a subject's eye along an optical axis to find the distribution of reflected light intensity along the depth of the subject's eye. FD-OCT is further classified into a spectral domain type (SD-OCT) and a swept source type (SS-OCT). According to SD-OCT, a coherent light coming from an interferometer is resolved into wavelength spectra using a spectroscope consisting of a diffraction grating, detects the wavelength spectrum using a line sensor (eg. CCD camera), and inverse-fourier transform performs on a detection signal to acquire the distribution of reflected light intensity in the depth direction. According to SS-OCT, a spectrum signal is detected by scanning at light frequencies (wavelength) of a light source at high speed and measuring a signal from a photo detector (photodiode) in terms of time, and the inverse-fourier transform performs on this detection signal to obtain the distribution of reflected light intensity in the depth direction.

According to TD-OCT, information at one point with one measurement light can be acquired, while according to FD-OCT, all information in the depth direction with one measurement light can be acquired. Thus, FD-OCT can be greatly reduced time for measurement than TD-OCT. For this reason, FD-OCT is used for anterior ocular segment OCT to enable three-dimensional analysis.

In general, according to OCT, the measurement light one-dimensionally scan the subject's eye to acquire a two-dimensional tomographic image (B-scan), and the two-dimensional tomographic images are repeatedly acquired while displacing the measurement light with respect to the subject's eye to acquire a three-dimensional image (C-scan).

Scanning methods include raster scan and radial scan. According to raster scan, one-dimensional scan (B-scan) is repeated along a horizontally extending scan line while shifting in the vertical direction (C-scan) to take a three-dimensional image of an eyeball (C-scan). This can acquire the tomographic image along each scan line. According to radial scan, one-dimensional scan (B-scan) along a radially-extending scan line (B-scan) is repeated while shifting in the circumferential direction (C-scan). This can acquire the tomographic image along each scan line.

For example, an anterior ocular segment optical coherence tomographic imaging device using such OCT includes a tomographic image acquisition means that acquires a tomographic image of an anterior ocular segment of a subject's eye in a depth direction along a scan line by optical coherence tomography, an imaging means that takes a front image of the subject's eye, and a cornea apex position detection means that detects position of an apex of a cornea of the subject's eye (for example, refer to Japanese Unexamined Patent Publication No. 2009-142313). In recent years, an anterior ocular segment optical coherence tomographic imaging device that can also image a back face of the crystalline lens of the anterior ocular segment has been proposed. This device can determine the degree of an intraocular lens inserted after a surgery of a cataract based on the acquired image of the crystalline lens (for example, refer to International Publication No. 2013/187361).

SUMMARY

However, there has not been proposed yet an anterior ocular segment optical coherence tomographic imaging device that can accurately analyze the shape of the crystalline lens. When the anterior ocular segment optical coherence tomographic imaging device images the anterior ocular segment, according to the Snell's law, the measurement light is refracted at the boundary of each of tissues (front and back faces of the cornea, front and back faces of the crystalline lens, and the like) in the anterior ocular segment, causing a distortion in the acquired tomographic image. The crystalline lens includes layers of cortex lentis and nucleus lentis. The different layers have different refractive indices, causing a distortion of the crystalline lens. In order to accurately analyze the shape of the crystalline lens, it is needed to identify the boundary of each layer of the crystalline lens, and to correct the distortion of the tomographic image based on the refractive index of each layer.

An object of the present invention is to provide an anterior ocular segment optical coherence tomographic imaging device and an optical coherence tomographic imaging method that can identify the boundary of each layer in the crystalline lens from the tomographic image to analyze the shape of the crystalline lens accurately.

To attain the above object, an anterior ocular segment optical coherence tomographic imaging device of the present invention is an anterior ocular segment optical coherence tomographic imaging device for taking a tomographic image of an anterior ocular segment including a crystalline lens of a subject's eye by optical coherence, the device including a layer boundary detection means configured to calculate brightness gradients from brightness values in a depth direction of the tomographic image from a cornea to a retina, detect an edge that is larger than a predetermined threshold, and identify a boundary of each layer of the crystalline lens from the position of the edge.

Through studies to attain the above object, the inventors have found a solution by noting, in the tomographic image, a variation in brightness along the depth, which occurs at the boundary of each layer of the crystalline lens, that is, 1) front and back faces of the crystalline lens are linear, and 2) a portion of the nucleus lentis in the normal eye appears black (has a low brightness). That is, the layer boundary detection means can find brightness values of the acquired tomographic image in the depth direction from the cornea to the retina (A-scan), calculate brightness gradients from the brightness values to detect an edge that is larger than a predetermined threshold, and identify a boundary of each layer of the crystalline lens. In this embodiment, a peak refers to the position of an apex of the image brightness information, and an edge refers to information found by processing the image brightness information by an edge filter, which identifies changes in brightness value.

The layer boundary detection means may be configured to identify a position of a falling edge of the brightness gradient in a region on a front face-side of the crystalline lens as a front surface of the nucleus lentis, and a position of a rising edge of the brightness gradient in a region on a back face-side of the crystalline lens as a back surface of the nucleus lentis. This can accurately identify positions of the front and back faces of the nucleus lentis.

The device may further include a tomographic image correction means configured to correct a distortion caused by refraction at the boundary of each layer of the crystalline lens by tracking a ray based on information on a refractive index of each layer of the crystalline lens in the tomographic image. As described above, the measurement light is refracted at the boundary of each tissue in the anterior ocular segment according to the Snell's law. Accordingly, the refractive index varies at the boundaries of the layers (front and back faces of the crystalline lens and front and back faces of the nucleus lentis) in the crystalline lens, causing a distortion of the crystalline lens in the acquired tomographic image. Thus, the tomographic image correction means can accurately analyze the shape of the crystalline lens.

The device may further include a first opacity detection means that determines the opacity of the crystalline lens based on the number of edges detected by the layer boundary detection means. As described in detail later, when the crystalline lens is turbid (in the case of the cataract eye), more edges are detected than the normal eye. The first opacity detection means determines presence or absence of the cataract and the grade of the cataract.

The device may further include a second opacity detection means configured to determine opacity of the crystalline lens by determining whether or not a sum and/or an average of the brightness values in the layer detected in the tomographic image is larger than a predetermined threshold. As described in detail later, in the tomographic image, the brightness value in the layer is large in the tomographic image of the eye having a severe cataract, while the brightness value in the layer is small in the tomographic image of the eye having a mild cataract. The second opacity detection means can quantitatively estimate the grade of the cataract based on the sum or average of the brightness values. As described above, the first opacity detection means can determine the opacity of the crystalline lens based on the number of edges detected by the layer boundary detection means. However, in some subject's eyes, the opacity of the crystalline lens may be too high, making edge detection difficult. Even in such case, the second opacity detection means can determine the opacity using the sum or the average of brightness values in the identified layer.

An optical coherence tomographic method of the present invention is an optical coherence tomographic imaging method for taking a tomographic image of an anterior ocular segment including a crystalline lens of a subject's eye by optical coherence, the method including a layer boundary detection step of calculating brightness gradients from brightness values in a depth direction of the tomographic image from a cornea to a retina, detecting an edge that is larger than a predetermined threshold, and identifying a boundary of each layer of the crystalline lens as a position of the edge. This can identify the boundary of each layer of the crystalline lens in the acquired tomographic image more easily.

In this case, the layer boundary detection step may identify a position of a falling edge of the brightness gradient in a region on a front face-side of the crystalline lens as a front surface of the nucleus lentis, and a position of a rising edge of the brightness gradient in a region on a back face-side of the crystalline lens as a back surface of the nucleus lentis, thereby identifying the front and back faces of the nucleus lentis.

The method may further include a tomographic image correction step of correcting a distortion caused by refraction at the boundary of each layer of the crystalline lens by tracking a ray based on information on a refractive index of each layer of the crystalline lens in the tomographic image. This can correct the distortion of the tomographic image, which is caused by refraction of the measurement light, and accurately analyze the shape of the crystalline lens.

The method may further include a first opacity detection means that determines the opacity of the crystalline lens based on the number of edges detected by the layer boundary detection means and a second opacity detection step of determining opacity of the crystalline lens by determining whether a sum and/or an average of the brightness values in the layer detected in the tomographic image is larger than a predetermined threshold. This can determine the opacity of each layer of the crystalline lens relatively to easily determine the presence or absence and the grade of the cataract.

The anterior ocular segment optical coherence tomographic imaging device and the optical coherence tomographic imaging method according to the present invention can readily identify the boundary of each of the layers (cortex lentis and nucleus lentis) of the crystalline lens based on brightness information on the tomographic image.

BRIEF DESCRIPTION OF DRAWINGS

FIG. 7A is a tomographic image of an anterior ocular segment before correction of refraction, and FIG. 7B is a tomographic image of an anterior ocular segment after correction of refraction.

DETAILED DESCRIPTION

Figure 1:
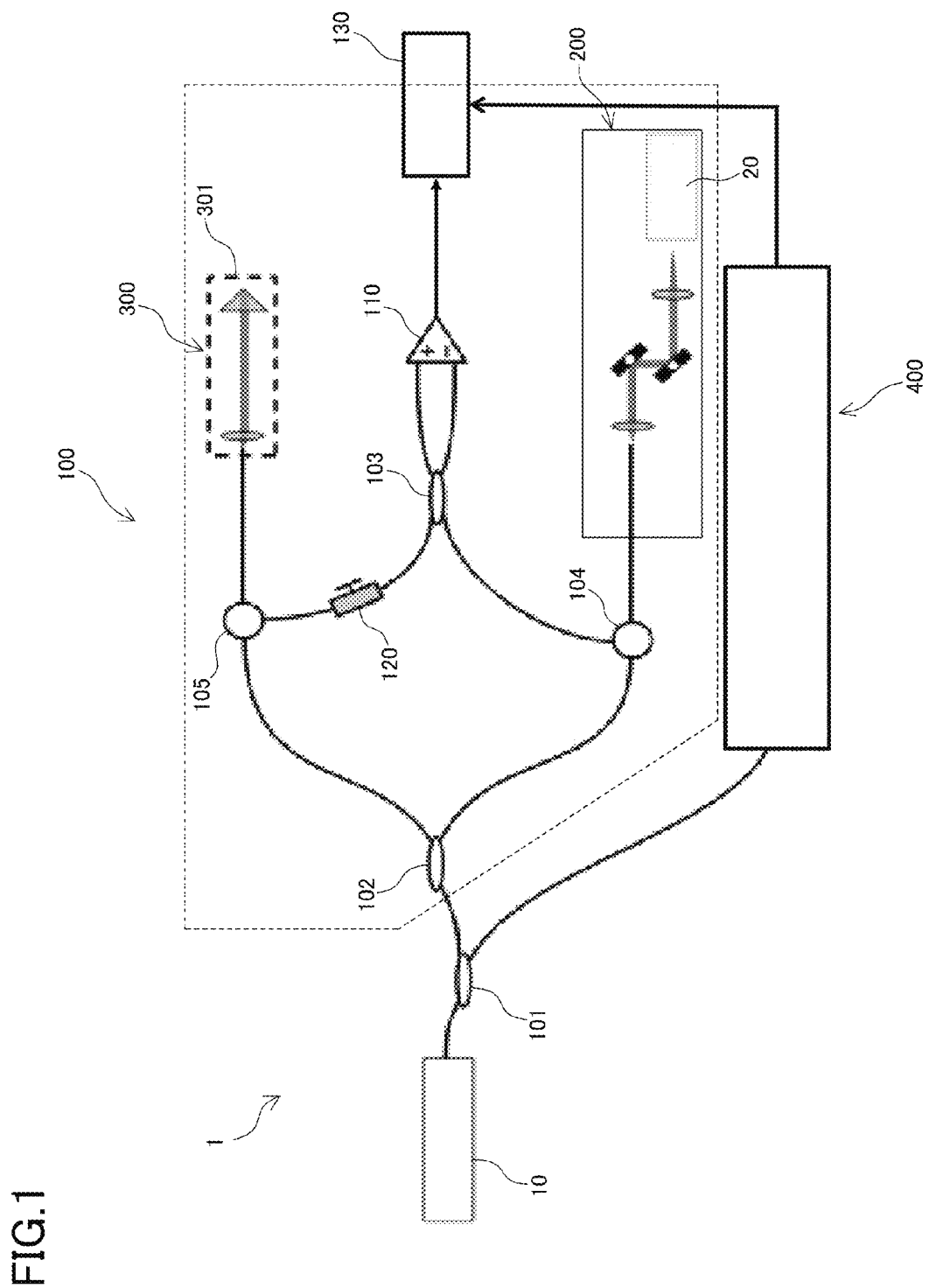
FIG. 1 is a schematic view illustrating configuration of an anterior ocular segment optical coherence tomographic imaging device in accordance with an embodiment.

An embodiment of the present invention will be described below with reference to figures. FIG. 1 illustrates configuration of an optical coherence tomographic imaging device 1 of the present invention. The optical coherence tomographic imaging device 1 mainly includes an OCT coherence system 100 and a K-clock generating coherence optical system 400.

The OCT coherence system 100 acquires a tomographic image of an anterior ocular segment of a subject's eye according to optical coherence tomography. This embodiment adopts SS-OCT, and a light source 10 is a wavelength sweeping light source that varies wavelength with time for scanning. The wavelength sweeping light source can perform high-speed scan with a band having a central wavelength of 1 μm or more and a sweep width of 70 nm or more at 50 kHz or higher. Input light emitted from the light source 10 is guided by an optical fiber such as a single mode fiber, and is used for taking a tomographic image of a sample 20 and generating a k-clock. An SMFC (single mode fiber coupler) 101 that branches the emitted input light is provided among the light source 10, and the OCT coherence system 100 and the K-clock generating coherence optical system 400. The SMFC 101 branches the input light toward the OCT coherence system 100 and the K-clock generating coherence optical system 400.

The OCT coherence system 100 includes an SMFC 102 that further branches the branched input light, a scanning-alignment optical system 200 that measures the sample 20 using one further branched input light as measurement light, a reference optical system 300 using the other further branched input light as reference light, an SMFC 103 that combines light reflected on the sample 20 with the reference light into measurement coherent light, a balanced detector 110 that receives measurement coherent light combined by the SMFC 103 to output a measurement coherence signal, and an arithmetic processing section 130 that acquires a tomographic image of the sample 20 according to arithmetic processing based on the measurement coherence signal.

The SMFC 102 receives the one input light branched by the SMFC 101, and further branches the input light into the lights which guided by the incident input light to the scanning-alignment optical system 200 and the reference optical system 300.

The scanning-alignment optical system 200 is an optical system that irradiates the sample 20 with the measurement light via a measurement-side circulator 104, and guides the light reflected on the sample 20 to the SMFC 103. Details of the scanning-alignment optical system 200 will be described later.

The measurement-side circulator 104 is an optical element disposed among the SMFC 102, the scanning-alignment optical system 200, and the SMFC 103. The measurement light guided to the SMFC 102 via the measurement-side circulator 104 is guided to the scanning-alignment optical system 200, and the reflected light guided from the scanning-alignment optical system 200 is guided to the SMFC 103.

The reference optical system 300 includes a reference section 301 that converts the input light into the reference light, and a reference-side circulator 105 that guides the input light to the reference optical system 300 and guides the reference light to the SMFC 103. In this embodiment, the reference section 301 is a prism that emits the incident input light entered as the reference light. The reference section 301 is movable such that an optical path length of the scanning-alignment optical system 200 is matched to an optical path length of the reference optical system 300 before measurement of the sample 20. During measurement of the sample 20, the position of the reference section 301 is fixed.

The reference-side circulator 105 is an optical element disposed among the SMFC 102, the reference section 301, and the SMFC 103. The input light guided from the SMFC 102 via the reference-side circulator 105 is guided to the reference section 301, and the reference light guided from the reference section 301 is guided to the SMFC 103.

The SMFC 103 combines the reflected light guided from the scanning-alignment optical system 200 with the reference light guided from the reference optical system 300 to generate the measurement coherent light, and branches the combined measurement coherent light into two light beams of the measurement coherent light, which differ from each other in phase by 180°, to the balanced detector 110.

The balanced detector 110 is an optical detector that receives the measurement coherent light combined by the SMFC 103. The SMFC 103 is disposed among the scanning-alignment optical system 200, the reference optical system 300, and the balanced detector 110, and a polarization controller 120 is disposed between the reference optical system 300 and the SMFC 103.

The polarization controller 120 is an element that controls polarization of the reference light guided from the reference optical system 300 to the SMFC 103. The polarization controller 120 may be any well-known type such as in-line type and paddle type, and is not specifically limited.

The arithmetic processing section 130 acquires the tomographic image of the sample 20 by arithmetic processing based on the measurement coherence signal outputted from the balanced detector 110, and displays the acquired tomographic image on a monitor. The arithmetic processing section 130 performs functions of a layer boundary detection means, a tomographic image correction means, and first and second opacity detection means, which are main features of the present invention.

Figure 2:
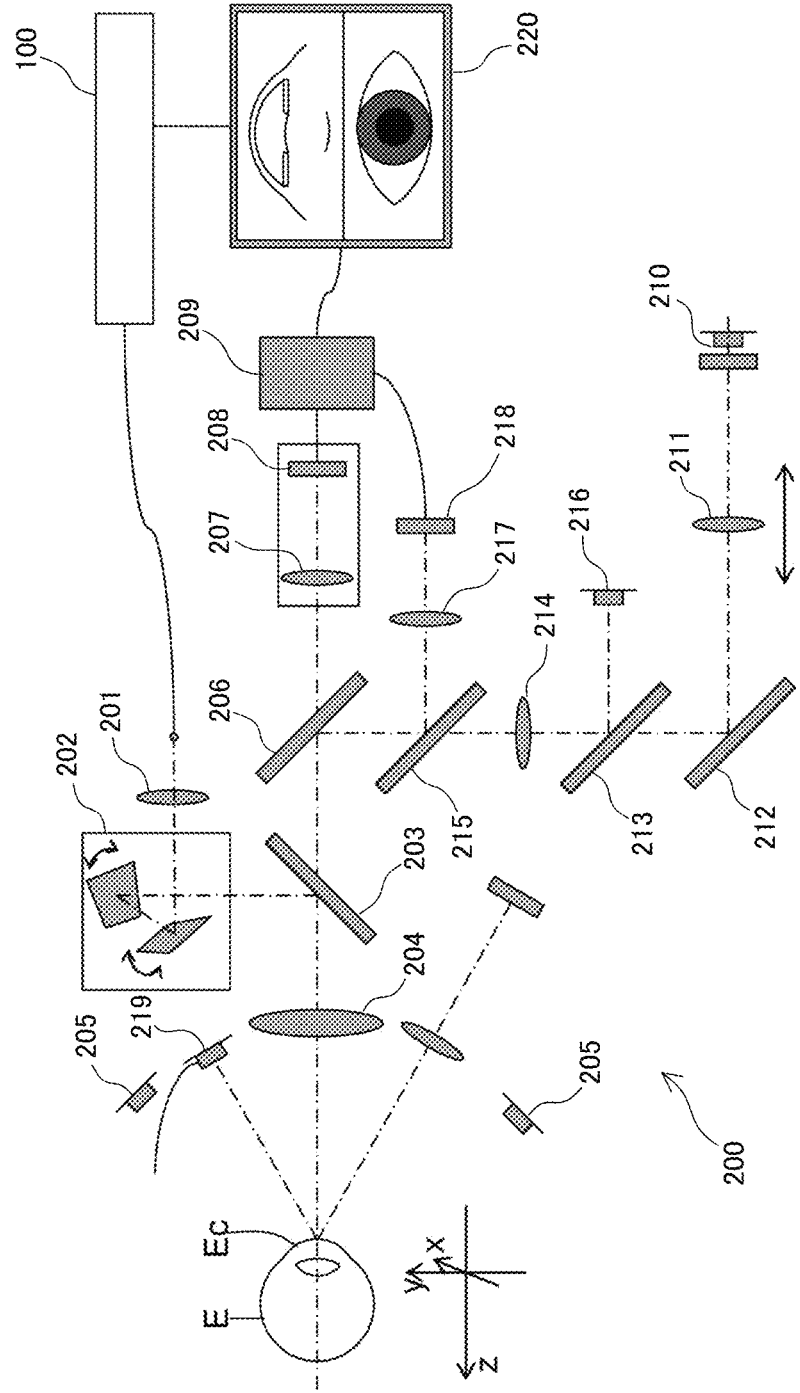
FIG. 2 is a schematic view illustrating configuration of a scanning-alignment optical system in FIG. 1.

FIG. 2 illustrates configuration of a scanning-alignment optical system 200. The scanning-alignment optical system includes a scanning optical system, an anterior ocular segment imaging system, a fixation mark optical system, and an alignment optical system.

In the scanning optical system, the measurement light outputted from the SMFC 102 is inputted from the measurement-side circulator 104, and is further inputted from the measurement-side circulator 104 to a galvano-scanner 202 via a collimator lens 201. The galvano scanner 202 serves to scan the sample with the measurement light, and is driven by a galvano-driver not illustrated.

The measurement light outputted from the galvano-scanner 202 is reflected on a hot mirror 203 by 90°, and is entered on a subject's eye E through an objective lens 204. The measurement light incident reflected on each of tissues (the cornea, the anterior chamber, the iris, the crystalline lens, and so on) of the anterior ocular segment Ec, the reflected light passes the objective lens 204, the hot mirror 203, the galvano-scanner 202, and the collimator lens 201 in an order opposite to the above-mentioned order, and is inputted to the SMFC 103 via the measurement-side circulator 104.

Then, the SMFC 103 combines the reflected light from the anterior ocular segment Ec with the reference light, and inputs its signal to the balanced detector 110. The balanced detector 110 measures coherence for each wavelength, and inputs the measured measurement coherence signal to the arithmetic processing section 130. Then, the arithmetic processing section 130 inverse-fourier transform is applied to the measurement coherence signal to acquire a tomographic image of the anterior ocular segment Ec along a scan line, and displays the tomographic image on a monitor 220.

The anterior ocular segment imaging system includes illumination light sources 205, 205, the objective lens 204, a hot mirror 203, a cold mirror 206, an imaging lens 207, a CCD camera 208, and an optical control section 209. The illumination light sources 205, 205 irradiate a front face of the subject's eye E with illumination light in a visible light region, and light reflected on the subject's eye E passes the objective lens 204, the hot mirror 203, the cold mirror 206, and the imaging lens 207 and enters into the CCD camera 208. Thereby, a front image of the subject's eye E is taken, and taken image data is processed by the optical control section 209, and the processed image is displayed on the monitor 220.

The fixation mark optical system enables the subject to view a fixation light so as not to move an eyeball (subject's eye E) as much as possible, and includes a fixation mark light source 210, a variable-focus movable lens 211, a cold mirror 212, a cold mirror 213, a relay lens 214, a half mirror 215, the cold mirror 206, the hot mirror 203, and the objective lens 204. Thereby, light outputted from the fixation mark light source 210 passes the variable-focus movable lens 211, the cold mirror 212, the cold mirror 213, relay lens 214, the half mirror 215, the cold mirror 206, the hot mirror 203, and the objective lens 204 in this order, and is outputted toward the subject's eye E. The variable-focus movable lens 211 is movable to make the focus of the fixation mark variable. That is, by moving the variable-focus movable lens 211 to any position, for example, by moving the variable-focus movable lens 211 such that the fixation mark is in focus at a position corresponding to the optical power value the subject's eye, measurement can be made in the state where the subject can naturally view the fixation mark (no load on the crystalline lens). In use for study on the focus adjustment function of the crystalline lens, images of the crystalline lens in the natural viewing state, and in the loaded state in which an adjustment load is applied to the crystalline lenses such that the fixation mark is in focus at a closer position than the natural viewing state by moving the variable-focus movable lens 211, can be taken to compare the images of the crystalline lens in shape. Further, the state where the shape is changing with gradually moving the variable-focus movable lens 211 can be imaged in animation.

The alignment optical system includes an XY-direction position detection system that detects the position of the subject's eye E (apex of the cornea) in an XY direction (vertical and horizontal displacements with respect to a main body), and a Z-direction position detection system that detects the position of the subject's eye E (apex of the cornea) in a frontward and backward direction (Z direction).

The XY-direction position detection system includes an XY-position detection light source 216, the cold mirror 213, the relay lens 214, the half mirror 215, the cold mirror 206, the hot mirror 203, the objective lens 204, an imaging lens 217, and a two-dimensional position sensor 218. The XY-position detection light source 216 emits alignment light for position detection toward the anterior ocular segment Ec (cornea) of the subject's eye E via the cold mirror 213, the relay lens 214, the half mirror 215, the cold mirror 206, the hot mirror 203, and the objective lens 204.

Since the surface of the cornea of the subject's eye E is spherical, the alignment light is reflected on the surface of the cornea so as to form a luminous point image at the inner side of the apex of the cornea, and the reflected light is entered from the objective lens 204. The reflected light (luminous point) from the apex of the cornea is inputted to the two-dimensional position sensor 218 via the objective lens 204, the hot mirror 203, the cold mirror 206, the half mirror 215, and the imaging lens 217. The two-dimensional position sensor 218 detects the position of the luminous point, thereby detecting the position (position in the X direction and the Y direction) of the apex of the cornea.

A detection signal of the two-dimensional position sensor 218 is inputted to the optical control section 209. In this case, the two-dimensional position sensor 218 is aligned with the anterior ocular segment imaging system, and a determined (normal) image acquisition position (position to be tracked at acquisition of the tomographic image) of the cornea apex is set. Examples of the normal image acquisition position of the cornea apex include a point that matches the center of an image taken by the CCD camera. Then, a two-dimensional position sensor 38 finds displacements of the detected position of the cornea apex (luminous point) in the X direction and the Y direction with respect to the normal position.

The Z-direction position detection system includes a Z-position detection light source 219, an imaging lens 220, and a line sensor 221. The Z-position detection light source 219 diagonally irradiates the subject's eye E with detection light (slit light or spot light), and diagonal light reflected on the cornea is entered on the line sensor 221 via the imaging lens 220. Here, varying the subject's eye E in the forward-backward direction (Z direction) varies the incidence position of the reflected light incident onto the line sensor 221, detecting the position of the subject's eye E in the Z direction.

Although not illustrated herein, the main body of the anterior ocular segment optical coherence tomographic imaging device 1 is supported by a holding table so as to be movable in the X direction (horizontal direction), the Y direction (vertical direction), and the Z direction (forward-backward direction). The main body is movable with respect to the holding table in the X direction, the Y direction, and the Z direction under control of a controller including a microcomputer having a CPU, memory, and so on. A front face (subject side) of the main body is fixedly provided with a jaw reception portion on which the subject's jaw is placed and a forehead contact portion against which the subject's forehead contacts, such that the eye of the subject (subject's eye E) is opposed to a front face of an inspection window on the front face of the main body. Then, the main body is moved with respect to the holding table based on displacements of the cornea apex (luminous point) in the X direction and the Y direction, which are detected by the XY-direction position detection system, and a displacement of the subject's eye E, which is detected by the Z-direction position detection system, such that all of the displacements become 0.

The k-clock generating coherence optical system 400 optically generates a sample clock (k-clock) from the input light branched from the SMFC 101 to sample the measurement coherence signal at regular frequency intervals (equal frequency spacing of the optical frequency). The k-clock signal thus generated is outputted toward the arithmetic processing section 130. This can suppress a distortion of the measurement coherence signal, preventing degradation of resolution.

Next, a layer boundary detection means, a tomographic image correction means, and an opacity detection means that are main features of the present invention will be described below. These means perform their functions in the above-described arithmetic processing section 130.

Figure 3:
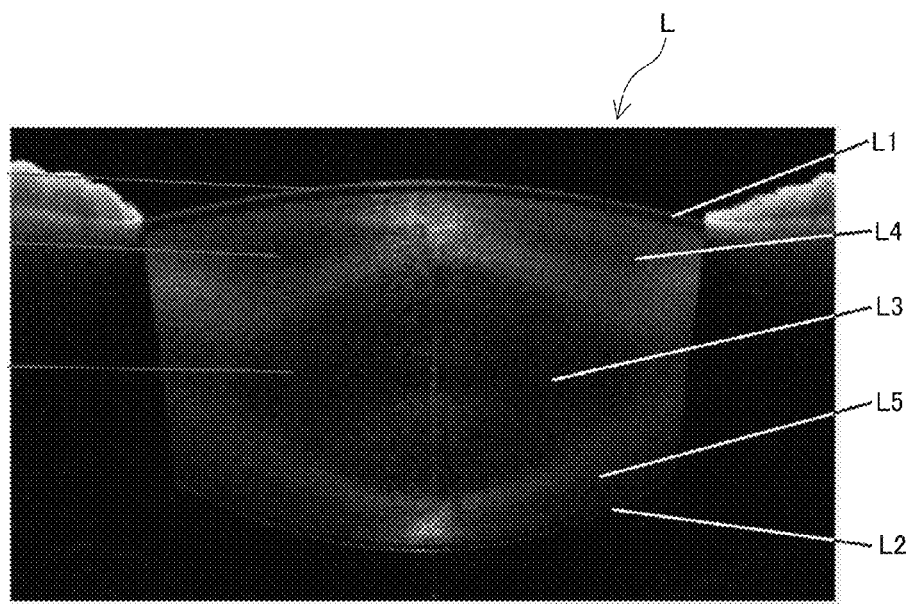
FIG. 3 is a tomographic image of a crystalline lens of a normal eye.

The layer boundary detection means identifies the boundary of each layer of the crystalline lens in a taken tomographic image of the subject's eye. FIG. 3 illustrates a tomographic image of a crystalline lens L of a normal eye. The tomographic image consists of plural A-scans. Thus, the layer boundary of the crystalline lens is identified by acquiring brightness information on each A-scan constituting the tomographic image. As illustrated in FIG. 3, in the tomographic image of the normal eye, a crystalline lens front face L1 and a crystalline lens back face L2 are represented as lines, and a nucleus lentis L3 located at the substantially center of the crystalline lens L appears black as a low-brightness region. A cortex lentis L4 located between the crystalline lens front face 1 and the nucleus lentis L3, and a cortex lentis L5 located between the crystalline lens back face L2 and the nucleus lentis L3 appear white as high-brightness regions. That is, the layer boundary detection means finds the brightness information on each A-scan from the tomographic image, and identifies the boundary of each layer in the crystalline lens based on the brightness information.

Figure 4:
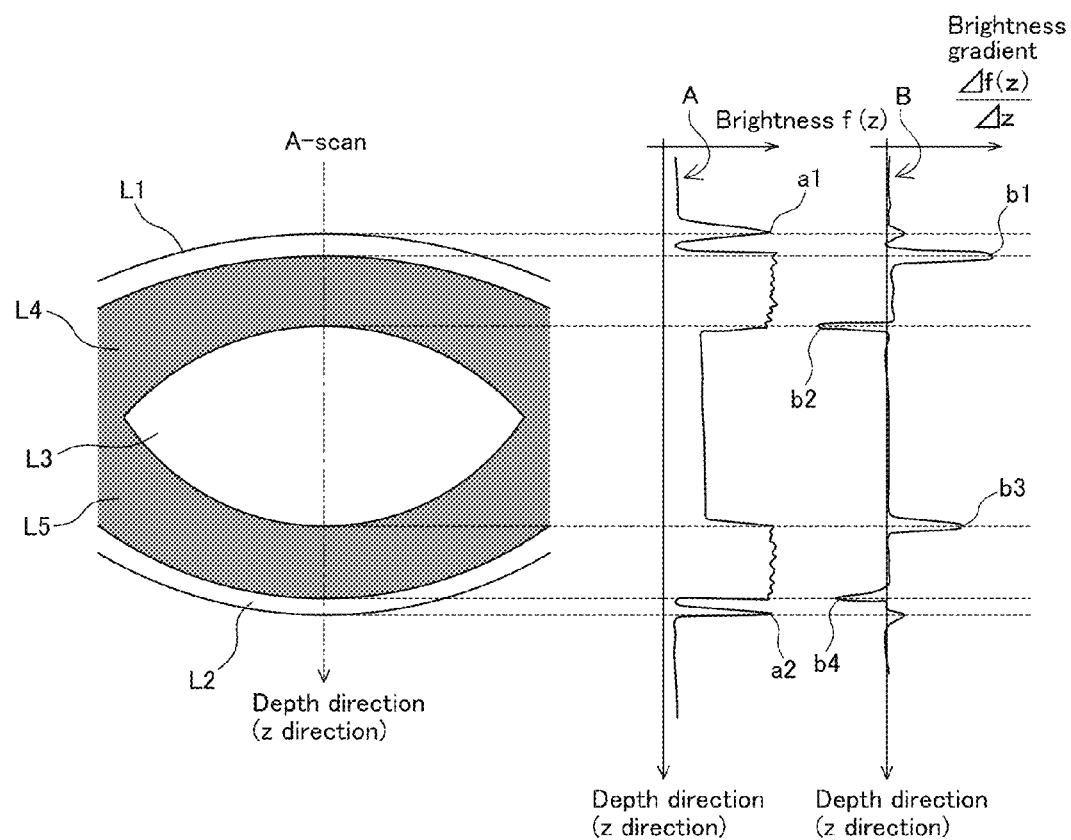
FIG. 4 a schematic view illustrating relationship between the tomographic image of the crystalline lens of the normal eye and distribution of brightness values f (z) and distribution of brightness gradients ($\Delta f(z)/\Delta z$) by one A-scan.

FIG. 4 schematic illustrates relationship between the tomographic image of the crystalline lens L of the normal eye and distribution of brightness values f(z) of one A-scan constituting the tomographic image (waveform graph A), and distribution of brightness gradient ($\Delta f(z)/\Delta z$) of the A-scan (waveform graph B). In this embodiment, a peak refers to a position of an apex of the image brightness information, and an edge refers to information found by processing the image brightness information by an edge filter, which identifies changes in brightness values. First, the layer boundary detection means detects the brightness values f(z) of the A-scan to acquire the waveform graph A as described in FIG. 4. Comparing the waveform graph A with the tomographic image, a large brightness value f(z) is detected in the white region that is the high-brightness region of the tomographic image. It turns out that a peak a1 of the waveform graph A corresponds to the position of the crystalline lens front face L1, and a peak a2 corresponds to the position of the crystalline lens back face L2. That is, the layer boundary detection means identifies the positions of the crystalline lens front face L1 and the crystalline lens back face L2 based on the peak a1 and the peak a2, respectively.

Subsequently, the brightness gradients ($\Delta f(z)/\Delta z$) are calculated from the brightness values f(z) to acquire the waveform graph B. Then, four edges b1, b2, b3, and b4 that are larger than a predetermined threshold are detected from the waveform graph B. When comparing the four edges with the tomographic image, the cortex lentis L4 is located between the rising edge b1 and the falling edge b2. Thus, the layer boundary detection means identifies the position corresponding to the falling edge b2 as the front face of the nucleus lentis L3. Similarly, since the cortex lentis L5 is located between the rising edge b3 and the falling edge b4, the position corresponding to the rising edge b3 is identified as the back face of the nucleus lentis L3. In this manner, the layer boundary detection means identifies the front and back boundaries of the nucleus lentis L3.

Based on information on the peaks and the edges that are acquired from the A-scan as described above, boundary faces between the crystalline lens front face L1 and the cortex lentis L4, between the cortex lentis L4 and the nucleus lentis L3, between the nucleus lentis L3 and the cortex lentis L5, and between the crystalline lens back face L2 and the cortex lentis L5 are traced.

The tomographic image correction means corrects a distortion of the tomographic image based on the identified information on the boundary of the layer of the crystalline lens and the refractive index of each layer. As discussed above, the measurement light is refracted on the face of the cornea as well as the boundary of each layer of the crystalline lens. The tomographic image correction means corrects the tomographic image with respect to the refraction. That is, a distortion caused by refraction on the layer boundaries is corrected by ray-tracing based on refractive index of each layer of the crystalline lens in the tomographic image. In this embodiment, since the refractive index varies depending on the age of the subject and the opacity of the crystalline lens of the subject's eye, an examiner sets the refractive index each time. A track of a ray is calculated based on the set refractive index according to the Snell's law to correct an angle distortion and optical distance, thereby correcting the distortion of the image. FIG. 7 illustrate tomographic images before and after correction, FIG. 7A illustrates the tomographic image before correction, and FIG. 7B illustrates the tomographic image after correction. Comparing the both tomographic images, the crystalline lens extends in the depth direction and becomes distorted in the tomographic image before correction, while the distortion is resolved in the tomographic image after correction.

The opacity detection means determines the opacity of the crystalline lens, and includes a first opacity detection means and a second opacity detection means.

Figure 5:
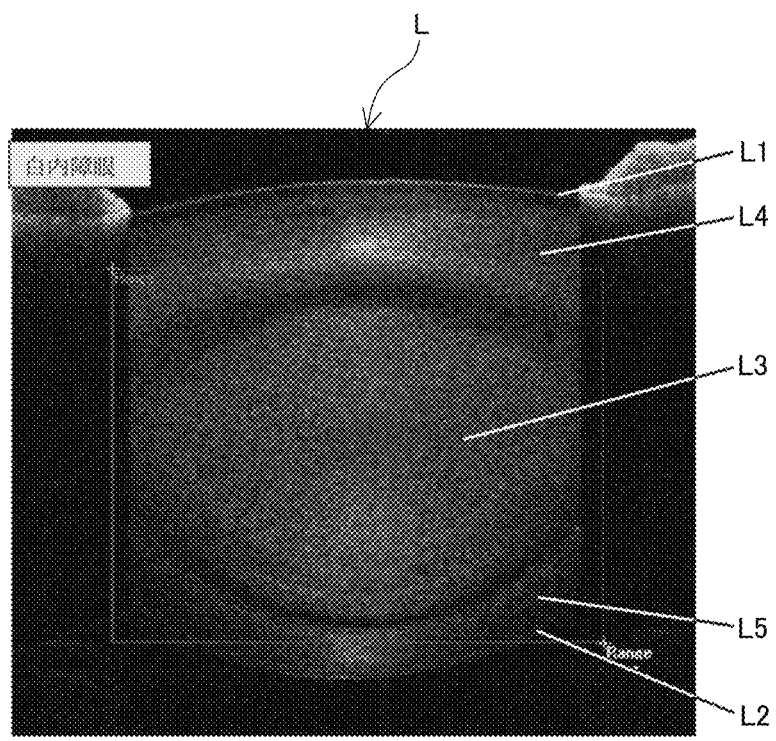
FIG. 5 is a tomographic image of a crystalline lens of a cataract eye.
Figure 6:
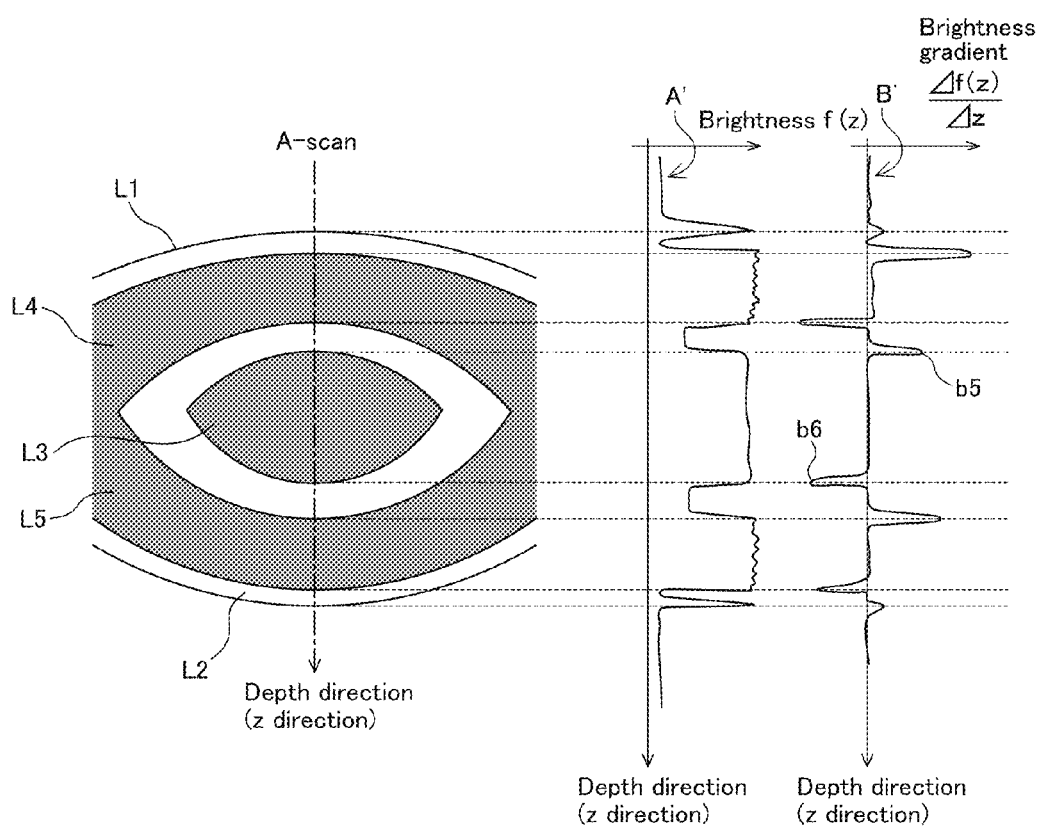
FIG. 6 a schematic view illustrating relationship between the tomographic image of the crystalline lens of the cataract eye and distribution of brightness values f (z) and distribution of brightness gradients ($\Delta f(z)/\Delta z$) by one A-scan.

The first opacity detection means determines the opacity of the crystalline lens based on the number of edges detected by the layer boundary detection means. FIG. 5 illustrates a tomographic image of a crystalline lens L of a nuclear cataract eye, and FIG. 6 schematically illustrate relationship between the tomographic image and distribution of brightness values f(z) of one A-scan of the crystalline lens (waveform graph A'), and distribution of brightness gradient ($\Delta f(z)/\Delta z$) (waveform graph B'). In FIG. 5, the nucleus lentis L3 appearing black as the low-brightness region in the normal eye appears white as a high-brightness region in the nuclear cataract eye. Thus, as illustrated in FIG. 6, the waveform graph A' detected by A scan in the tomographic image of the nuclear cataract eye has high brightness values in the nucleus lentis L3. As a result, in the waveform graph B', a rising edge b5 and a falling edge b6 which are not detected in the normal eye are detected. As described above, because the nuclear cataract eye has more detected edges than the normal eye, it can be determined whether the subject's eye is a cataract eye or not, and the grade of the cataract based on the number of edges. While the nuclear cataract is described in this embodiment, in the case of the cortical cataract, edges of the position corresponding to the affected sites are detected.

The second opacity detection means detects the opacity of the crystalline lens based on the brightness value. That is, the layer boundary detection means determines the grade of the cataract based on whether a sum or an average of the brightness values is larger or smaller than a predetermined threshold, or a difference between the sum or the average of the brightness values and the predetermined threshold. For example, in the nuclear cataract eye L as illustrated in FIG. 6, the boundary of the nucleus lentis L3 in the tomographic image is identified based on the edges b2 and b3. Then, a sum or an average of the brightness values in the identified region of the nucleus lentis L3 is calculated, and the sum or the average is compared with a predetermined threshold to find the opacity. This can quantitatively estimate the grade of the cataract, and determine the layer on which the cataract advances. In some subject's eyes, the opacity of the crystalline lens may be too high, making edge detection difficult. In such a case, the second opacity detection means can determine the opacity based on the sum or the average of the brightness values in the identified layer. While nuclear cataract is described in this embodiment, in the case of the anterior subcapsular cataract and the posterior subcapsular cataract, a white line (high-brightness line) is detected in the identified layer of the anterior subcapsule and the posterior subcapsule.

Figure 8:
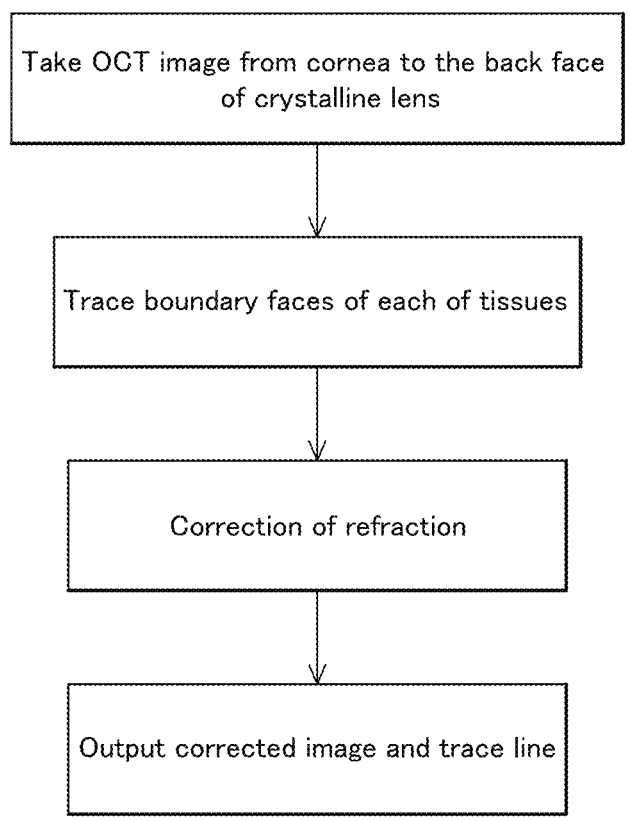
FIG. 8 is a flowchart of acquiring a tomographic image using the anterior ocular segment optical coherence tomographic imaging device in accordance with this embodiment.
Figure 9:
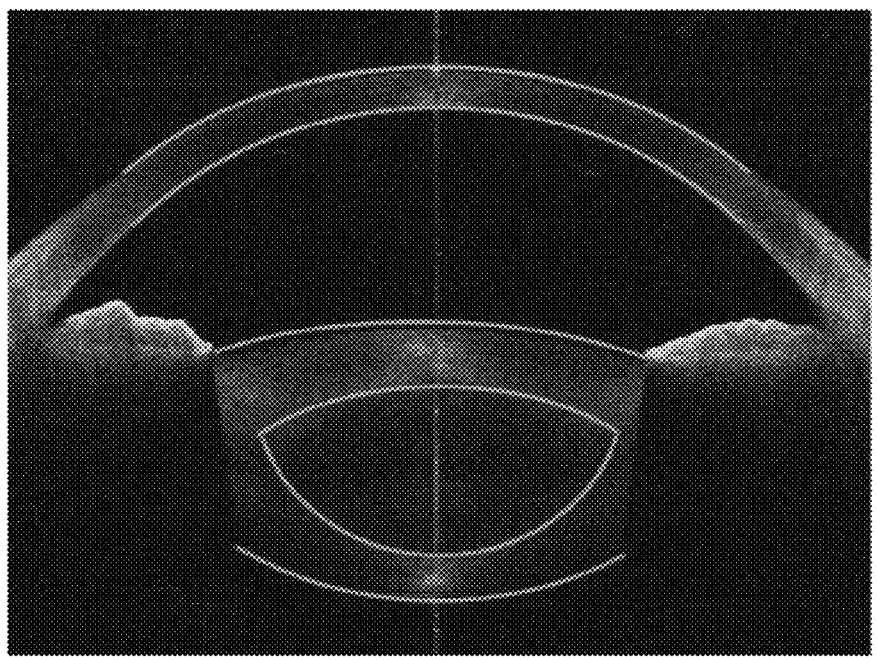
FIG. 9 is a tomographic image after correction of refraction, which is taken by using the anterior ocular segment optical coherence tomographic imaging device in accordance with this embodiment.

Next, a method for taking the tomographic image using anterior ocular segment optical coherence tomographic imaging device 1 will be described below. FIG. 8 illustrates a flowchart of acquiring a refraction-corrected image from the tomographic image of the subject's eye E using the optical coherence tomographic imaging device 1. First, the optical coherence tomographic imaging device 1 takes the tomographic image from the cornea and the back face of the crystalline lens. Then, the layer boundary detection means calculates distribution of the brightness values f (z) and distribution of brightness gradients ($\Delta f(z)/\Delta z$) of the tomographic image in the depth direction (A-scan) from the taken tomographic image, and identifies the boundaries of the layers in the crystalline lens based on the positions of the peaks and the edges to trace the boundary faces of tissues in the tomographic image. Next, the tomographic image correction means calculates the track of measurement light based on the refractive index set by the examiner, and corrects a distortion of the image to obtain an accurate tomographic image. Finally, this results in the accurate tomographic image that traces the boundary of each layer of the crystalline lens and has no distortion, as illustrated in FIG. 9. Further, the opacity detection means determines the opacity of the nucleus lentis to determine whether the subject's eye is a cataract eye or not, or the grade of the cataract.

The above-described anterior ocular segment optical coherence tomographic imaging device and anterior ocular segment optical coherence tomographic imaging method can readily identify the boundaries of the layers (the cortex lentis and the nucleus lentis) of the crystalline lens based on brightness information on the tomographic image. In addition, the distortion of the crystalline lens in the tomographic image due to refraction of the measurement light can be corrected to achieve an accurate tomographic image. Further, the opacity of the nucleus lentis can be readily determined based on the number of edges and/or the brightness value in the tomographic image.

In the above-mentioned embodiment, the OCT system 100 acquires the tomographic image according to SS-OCT and however, may use TD-OCT or SD-OCT in place of SS-OCT. The OCT system uses an optic fiber, and may be configured without the optic fiber.

In the above-mentioned embodiment, the examiner sets the refractive index each time in the tomographic image correction means. However, the present invention is not limited to this, and for example, a numerical value of the refractive index may be previously stored in the arithmetic processing section 130 and the numerical value may be called, or a numerical value stored according to the age or the opacity of a registered subject may be called.

In the above-mentioned embodiment, both the first opacity detection means and the second opacity detection means, and both the first opacity detection step and the second opacity detection step are provided and however, one of these means, and one of these steps may be adopted. The present invention may be modified in any suitable manner within the scope of the subject matter.

REFERENCE SIGNS LIST

1 Anterior ocular segment optical coherence tomographic imaging device
100 OCT system
200 Scanning-alignment optical system
A, A' Brightness distribution
B, B' Brightness gradient distribution
a1, a2 Peak
b1 to b6 Edge
L Crystalline lens
L1 Crystalline lens front face
L2 Crystalline lens back face
L3 Nucleus lentis
L4, L5 Cortex lentis

What is claimed is:

1. An anterior ocular segment optical coherence tomographic imaging device for taking a tomographic image of an anterior ocular segment including a crystalline lens of a subject's eye using optical coherence, the device comprising a layer boundary detector configured to calculate brightness gradients from brightness values in a depth direction of the tomographic image from a cornea to a retina, detect an edge that is larger than a predetermined threshold, and identify a boundary of each layer of the crystalline lens from position of the edge, and trace boundary faces between a crystalline lens front surface and a cortex lentis, between a crystalline lens back surface and the cortex lentis, and between the nucleus lentis and the cortex lentis in the tomographic image.

2. The anterior ocular segment optical coherence tomographic imaging device according to claim 1, wherein the layer boundary detector is configured to identify a position of a falling edge of the brightness gradient in a region on a front face-side of the crystalline lens as a front surface of the nucleus lentis, and a position of a rising edge of the brightness gradient in a region on a back face-side of the crystalline lens as a back surface of the nucleus lentis.

3. The anterior ocular segment optical coherence tomographic imaging device according to claim 1, further comprising a tomographic image corrector configured to correct a distortion caused by refraction at the boundary of each layer of the crystalline lens by tracking a ray based on information on a refractive index of each layer of the crystalline lens in the tomographic image.

4. The anterior ocular segment optical coherence tomographic imaging device according to claim 1, further comprising a first opacity detector configured to determine opacity of the crystalline lens based on the number of edges detected by the layer boundary detector.

5. The anterior ocular segment optical coherence tomographic imaging device according to claim 1, further comprising a second opacity detector configured to determine opacity of the crystalline lens by determining whether or not a sum and/or an average of the brightness values in the layer detected in the tomographic image is larger than a predetermined threshold.

6. The anterior ocular segment optical coherence tomographic imaging device according to claim 4, further comprising a second opacity detector configured to determine opacity of the crystalline lens by determining whether or not a sum and/or an average of the brightness values in the layer detected in the tomographic image is larger than a predetermined threshold.

7. An optical coherence tomographic imaging method for taking a tomographic image of an anterior ocular segment including a crystalline lens of a subject's eye by optical Coherence, the method comprising a layer boundary detection step of calculating brightness gradients from brightness values in a depth direction of the tomographic image from a cornea to a retina, detecting an edge that is larger than a predetermined threshold, and identifying a boundary of each layer of the crystalline lens as a position of the edge, and trace boundary faces between a crystalline lens front surface and a cortex lentis, between a crystalline lens back surface and the cortex lentis, and between the nucleus lentis and the cortex lentis in the tomographic image.

8. The optical coherence tomographic imaging method according to claim 7, wherein the layer boundary detection step identifies a position of a falling edge of the brightness gradient in a region on a front face-side of the crystalline lens as a front surface of the nucleus lentis, and a position of a rising edge of the brightness gradient in a region on a back face-side of the crystalline lens as a back surface of the nucleus lentis.

9. The optical coherence tomographic imaging method according to claim 7, further comprising a tomographic image correction step of correcting a distortion caused by refraction at the boundary of each layer of the crystalline lens by tracking a ray based on information on a refractive index of each layer of the crystalline lens in the tomographic image.

10. The anterior ocular segment optical coherence tomographic imaging method according to claim 7, further comprising a first opacity detection step of determining opacity of the crystalline lens based on the number of edges detected by the layer boundary detection step.

11. The anterior ocular segment optical coherence tomographic imaging method according to claim 7, further comprising a second opacity detection step of determining opacity of the crystalline lens by determining whether or not a sum and/or an average of the brightness values in the layer detected in the tomographic image is larger than a predetermined threshold.

12. The anterior ocular segment optical coherence tomographic imaging method according to claim 10, further comprising a second opacity detection step of determining opacity of the crystalline lens by determining whether or not a sum and/or an average of the brightness values in the layer detected in the tomographic image is larger than a predetermined threshold.

* * * * *